US007981663B2

(12) United States Patent
Sattler et al.

(10) Patent No.: US 7,981,663 B2
(45) Date of Patent: Jul. 19, 2011

(54) GROUP OF REAGENT CARRIERS THAT IS COMBINED TO FORM A COMPOSITE

(75) Inventors: Stephan Sattler, Stamberg (DE); Reinhold Krämer, Peissenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 376 days.

(21) Appl. No.: 12/168,584

(22) Filed: Jul. 7, 2008

(65) Prior Publication Data

US 2009/0011401 A1 Jan. 8, 2009

Related U.S. Application Data

(63) Continuation of application No. PCT/EP2007/000269, filed on Jan. 12, 2007.

(30) Foreign Application Priority Data

Jan. 13, 2006 (DE) ......................... 10 2006 001 882

(51) Int. Cl.
*C12M 3/00* (2006.01)

(52) U.S. Cl. ................................. 435/287.1; 435/288.4

(58) Field of Classification Search ......................... None
See application file for complete search history.

(56) References Cited

U.S. PATENT DOCUMENTS 4,786,601 A * 11/1988 Rothenberg ............... 435/305.2
4,960,219 A * 10/1990 Jordan et al. .................. 215/354
5,048,642 A 9/1991 Lloyd
5,112,574 A * 5/1992 Horton .......................... 422/569
5,128,104 A * 7/1992 Murphy et al. ............... 356/246
5,554,268 A * 9/1996 Priddy et al. .................. 204/400
5,616,301 A 4/1997 Moser et al.
5,722,553 A * 3/1998 Hovatter ...................... 220/23.8
5,795,547 A 8/1998 Moser et al.
5,830,344 A * 11/1998 Priddy et al. .................. 205/775
5,862,934 A * 1/1999 Sattler et al. ................ 220/23.4
6,558,632 B1 5/2003 Guller et al.
7,550,291 B2 6/2009 Belz et al.
2001/0036426 A1 11/2001 Kohrmann et al.
2004/0171141 A1 9/2004 Plank
2004/0234422 A1* 11/2004 Belz et al. ..................... 422/102

FOREIGN PATENT DOCUMENTS

| | | | |
|---|---|---|---|
| DE | 8337595 | * | 12/1983 |
| DE | 8337595 | | 3/1984 |
| DE | 10203940 | | 8/2003 |
| EP | 0100664 | | 2/1984 |
| EP | 0 290 019 A2 | | 5/1988 |
| EP | 0290019 | | 11/1988 |
| EP | 0834792 | | 4/1998 |
| WO | 99/44745 | | 9/1999 |
| WO | WO 99/44745 | * | 9/1999 |
| WO | 2005/012561 A1 | | 2/2005 |

OTHER PUBLICATIONS

Internal Search Report dated Feb. 5, 2007.

* cited by examiner

*Primary Examiner* — Ann Lam
(74) *Attorney, Agent, or Firm* — Dinsmore & Shohl LLP

(57) ABSTRACT

The invention concerns a group of reagent carriers that is combined to form a composite, each one of said carriers having at least one test region located in a shallow trough-like depression, where the reagent carriers in the composite are held together exclusively by interconnected protective covers for the test regions.

11 Claims, 3 Drawing Sheets

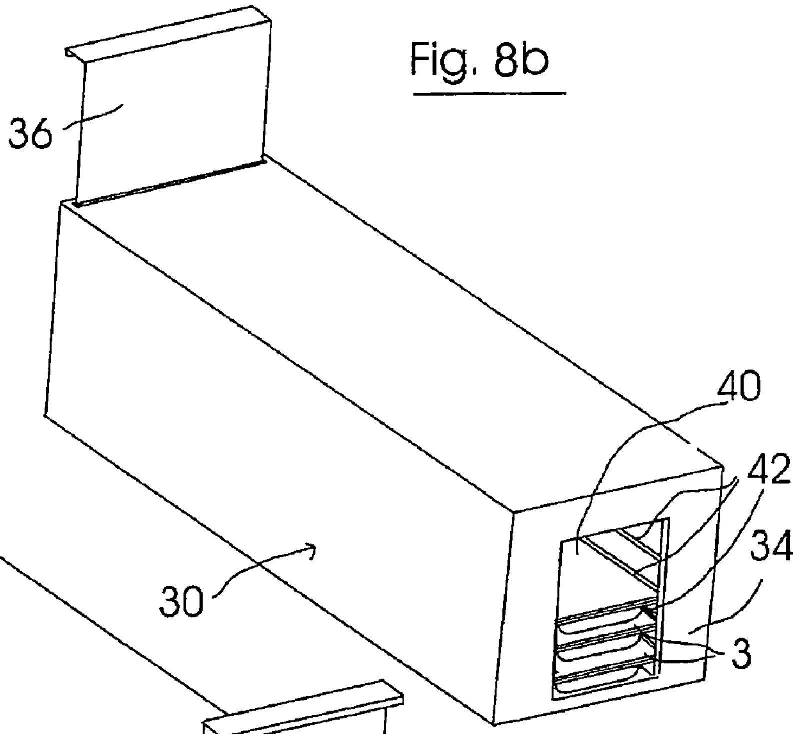
Fig. 8b
Fig. 8a
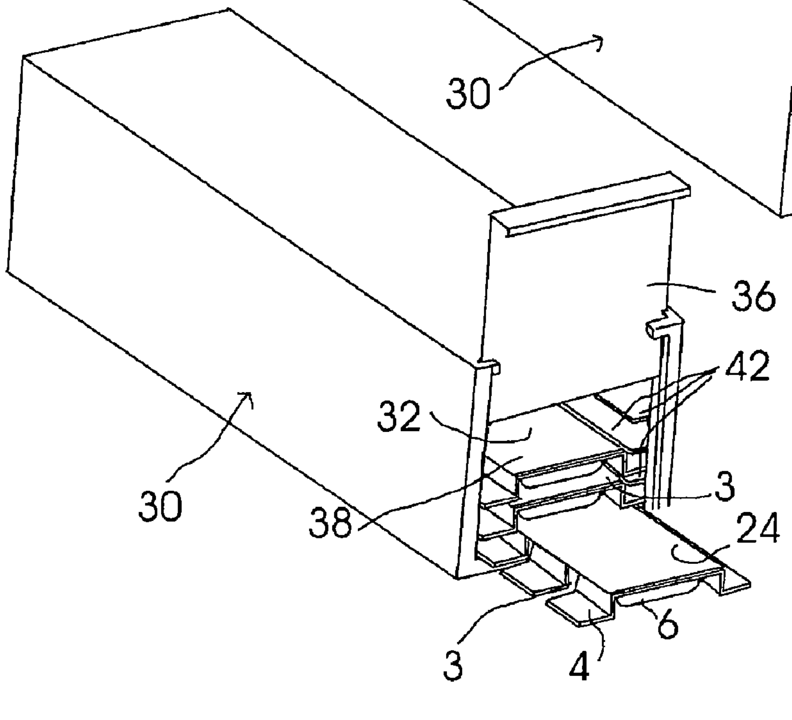

GROUP OF REAGENT CARRIERS THAT IS COMBINED TO FORM A COMPOSITE

CROSS REFERENCE TO RELATED APPLICATIONS

This application is a continuation of PCT application EP2007/000269, filed 12 Jan. 2007, which claims priority to German Application No. 10 2006 001 882.6, filed 13 Jan. 2006.

FIELD OF THE INVENTION

The invention concerns a group of reagent carriers that is combined to form a composite, each one of said carriers having at least one test region.

BACKGROUND OF THE INVENTION

Reagent carriers of the type that are under consideration here are test chips e.g. biochips for detecting analytes in a sample liquid. They can for example be used for immunoassay applications in which binding reactions between reactants which are in one embodiment immobilized on an area of a test region of the reagent carrier, and analytes which are present in a sample liquid wetting the test area are detected. These reagent carriers which are also referred to as chips in the following must be treated and handled in a protected manner until their intended use so that undesired contamination is avoided and the reactants retain their specific binding capability for the sample analytes.

The base housing of the reagent carriers can be formed from a variety of solid materials and especially also from plastic.

Such plastic chips can for example, after their manufacture in an injection molding process, be coated with "dry chemistry" for example using a microspot method in order to immobilize the reactant molecules on the test area of the chip. Such a coating usually takes place automatically in a coating plant. After the coating and drying the chips are prepared ready for use. They then have to be placed in a package which offers them protection against environmental influences.

Several weeks may indeed pass before the individual chips are used for medical or chemical investigations. Thus, high demands must be made on the measures for screening the test regions of the chips against environmental influences such as varying air humidity, varying temperature, dust etc.

Furthermore, it should be possible to automatically handle chips that are combined in groups in packaging stations and furthermore when the chips are used by customers in analyzers. The automated processes when the packaging is filled by the manufacturer and when the chips are used by customers should be designed to be as simple and space-saving as possible. It should be possible to handle the chips individually if needed when they are used to detect analytes in a sample liquid.

SUMMARY OF THE INVENTION

The present invention in one embodiment provides a method for preparing reagent carrier chips in such a manner that they are protected and can be handled in groups using relatively simple means in order to for example package them or convey them to an analyzer.

In another embodiment according to the invention, combined groups of reagent carriers each of which has at least one test region in a shallow trough-like depression or hollow to form composites is provided, wherein the reagent carriers in their composite are held together exclusively by interconnected protective covers for the test regions. In this connection embodiment, each reagent carrier is allocated a protective cover or section of a protective cover in such a manner that the test region of the reagent carrier is closed to the outside by the protective cover and is thus protected. Hence, the reagent carriers of a group are only connected by their protective covers and their connections. Such a composite of reagent carriers can be automatically handled in a simple manner and enables individual reagent carriers to be separated from the composite as required either by removing the said reagent carrier from its protective cover or by separating the reagent carrier with its protective cover from the remaining composite.

The protective covers are in one embodiment joined together to form a strip arrangement where the reagent carriers that are held together by the protective covers in the composite are arranged side-by-side to form a row corresponding to a strip arrangement. Such a strip arrangement of protective covers can for example be manufactured e.g. as a unit from one plastic in an injection-molding process. The amount of material required for this is extremely low. The composites of reagent carriers in a serial arrangement can be manually or automatically stacked in magazines. Likewise the connected rows of reagent carriers can be simply removed from such a magazine.

The reagent carriers each have a trough-like depression containing the test region which is closed from the outside by a protective cover. The bottom of this trough-like depression serves as a test area on which the reactants are immobilized. The trough-like depression can hold a small amount of sample liquid in a respective conventional analysis. The depth of the trough-like depression is in one embodiment less than its length or than its largest opening diameter.

As already mentioned the test regions and thus the trough-like depressions have, however, previously been closed by the protective covers. In this connection it is expedient according to one embodiment of the invention that the protective covers have a bulge which extends into the trough-like depression to near the bottom thereof, the bulge having an approximately complementary contour to that of the trough-shaped depression. Thus, there is a minimal volume of air space between the test region surface and the protective cover of a respective reagent carrier and hence this air space can only take up an extremely small amount of moisture. This is advantageous for the storage life of the reagent carriers.

According to a further embodiment of the invention each protective cover has at least one hollow space for holding a suitable desiccant for the reagent carrier to which it is allocated or for holding a chemical that is to be brought into contact with the reagent carrier. In the case of the variant described above with a bulged protective cover it in one embodiment has a hollow configuration where the hollow space defines the desiccant reservoir or chemical reservoir and for example has a communication opening or a pierceable predetermined break-through point in a wall separating it from the trough-like depression. The bulge is in one embodiment in the form of a thin walled embossing which is convex on the side facing the test region and concave on the side facing the outside where the concavity forms such a desiccant reservoir or chemical reservoir. This can be sealed towards the outside by means of a sealing foil such as laminated aluminum foil. Any other hollow space areas of the reagent carrier especially in the cover can also be used as a reservoir for liquid reagents or dry reagents which can be transported to the test region through optionally pre-prepared communication openings.

The protective covers and the reagent carriers in one embodiment have mutually complementary and mutually engaging snap connection means or clamp connection means which enable the reagent carriers to be detached from the protective cover as required but ensure that the protective cover and reagent carriers are securely held together when the composites are handled normally during packaging processes or transport processes. The connection means can have a sealing function. According to one embodiment of the invention the protective covers and the reagent carriers additionally have mutually complementary and mutually engaging sealing means or sealing geometries. These may for example be sealing lips or suchlike which have been manufactured in the injection-molding process integrated with the protective cover or the body of the reagent carrier. A stop face for the sealing lip can serve as a complementary element to a sealing lip. Special sealing rings or suchlike also come into consideration as sealing aids.

The composites of reagent carriers in one embodiment have a flat surface at a suitable position e.g. on the outside of the protective cover which is printed with information or on which information can be optionally printed or written. However, this does not preclude the fact that information can also be printed on curved sections of the surface of the reagent carriers.

Furthermore, it is proposed that the connections between the protective covers are designed such that they contain predetermined breaking points which enable reagent carriers with their protective covers to be separated as required from the remaining composite. Such a detachment can for example take place manually by applying a certain force or optionally mechanically using cutting tools or suchlike.

The rows of interconnected reagent carriers according to one embodiment of the invention can comprise different numbers of reagent carriers as required.

The rows of interconnected reagent carriers can be in one embodiment individually packaged in bag-like protective coverings made of foil such as aluminum foil or plastic foil.

A hollow profile bar magazine also comes into consideration as packaging for the rows of interconnected reagent carriers.

A magazine packaging with a magazine case for a predetermined number of rows of interconnected reagent carriers is provided in one embodiment. The end face of the magazine case has a slide-in/slide-out opening for the rows of interconnected reagent carriers. In the interior of the magazine case supporting and guiding elements for the rows of interconnected reagent carriers are arranged on two side walls running orthogonally to the end face with the drawer opening. These are in one embodiment grooves or rail-like shelves which support the individual rows of interconnected reagent carriers and guide them when they are inserted into or pulled out of the magazine case.

A further opening is in one embodiment provided on the end opposite to the front end with the drawer opening which enables a pushing or gripping tool to access the individual rows of interconnected reagent carriers. This tool can for example be a push rod which can push out individual or optionally several rows of interconnected reagent carriers from the magazine case. The front end openings of the magazine case can be provided with push flaps or suchlike.

The magazine case is in one embodiment made of plastic and serves as a protective packaging which has the special features mentioned above for facilitating the loading of rows of interconnected reagent carriers and the delivery of rows of interconnected reagent carriers from the magazine case where such a delivery can for example take place automatically in a customer's analytical system.

The invention is further elucidated in the following on the basis of embodiment examples with reference to the figures.

BRIEF DESCRIPTION OF THE DRAWINGS

FIGS. 8*a* and 8*b* show a magazine case for rows of interconnected reagent carriers according to the invention in two different perspective views.

DETAILED DESCRIPTION

Figure 1A:
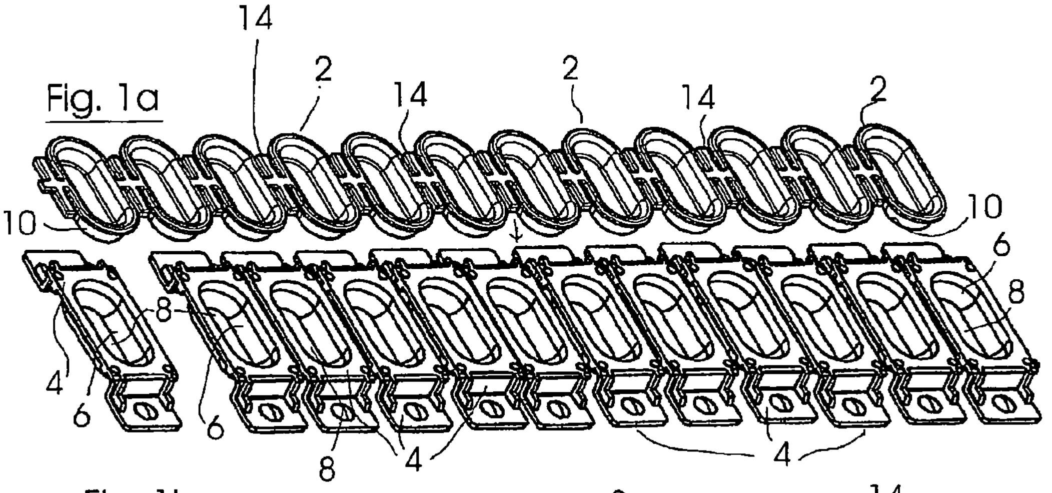
FIGS. 1*a* and 1*b* show in perspective diagrams elements of rows of interconnected reagent carriers in two different stages of preparing the rows of interconnected reagent carriers.

FIG. 1*a* shows a row of interconnected protective covers 2 and a group of individual reagent carriers 4 aligned in a row relative to one another which each have a trough-like depression 6 which should serve as a test region for detecting analytes in a sample liquid. As shown in particular in FIG. 2*c* the trough-like depressions 6 are relatively shallow in the sense that their depth t is less than their length l or than their largest opening diameter l. The reagent carriers 4 which still lie loosely next to one another in FIG. 1*a*, are brought together by the row of covers 2 resulting in the situation according to FIG. 1*b* and each trough-like depression 6 of the reagent carriers 4 is closed by a cover 2.

Figure 2A:
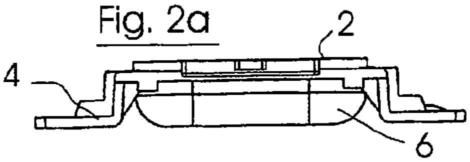
FIGS. 2*a*-2*c* show a reagent carrier of FIG. 1*b* in a side-view, a top-view and a cutaway side-view.
Figure 2B:
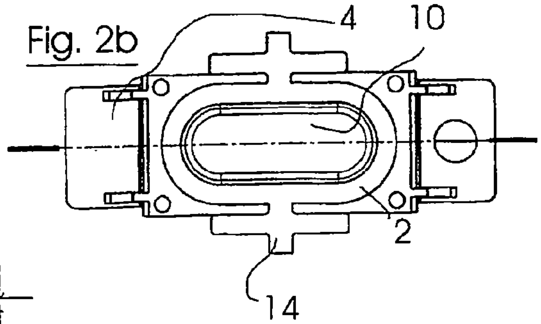
Figure 2C:
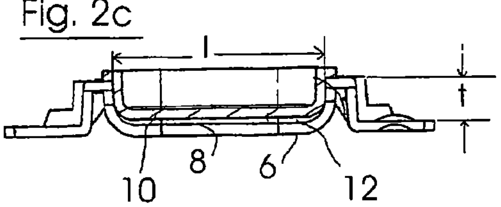

The covers 2 have a downwards directed convex bulge 10 which is approximately complementary to the contour of the trough-like depression 6 and is of such a size that it extends into the trough-like depression 6 in a clamping fit with a sealing function as shown especially in the longitudinal sectional view in FIG. 2*c*. Alternatively or in addition snap connection means could be provided which hold the covers 2 on the reagent carriers 4. Furthermore, additional or modified sealing elements could also be provided.

FIG. 2*c* also shows that the bulge 10 of the cover and the trough-like depression 6 are adapted to one another such that only a very small air space 12 remains above the bottom of the test region 8. The reduction of the air space 12 is advantageous in order to ensure that as little moisture as possible is enclosed when the reagent carriers 4 are capped. Reactants immobilized on the bottom of the test region 8 can thus be kept substantially dry until the reagent carriers 4 are used for analytical purposes.

Figure 1B:
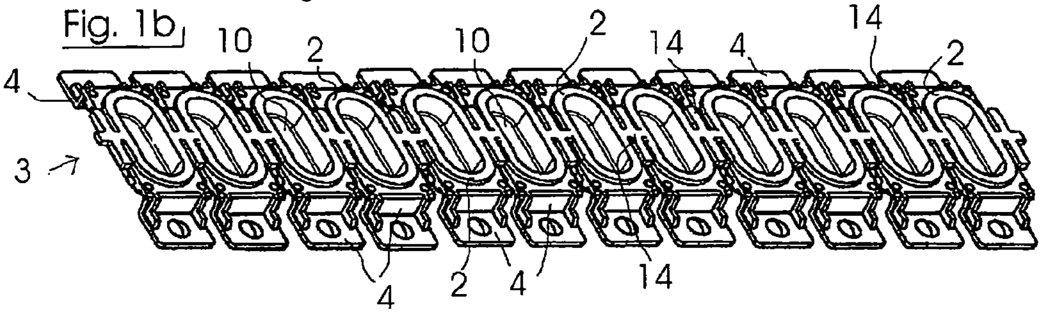

Since according to FIG. 1*b* the connecting sites 14 between the covers 2 are still present and are not interrupted, they produce a composite of reagent carriers 4 that can be handled uniformly. The reagent carriers 4 are thus kept together in the composite by the interconnected protective covers 2 for the test regions 6. Such a row 3 of interconnected reagent carriers according to FIG. 1*b* can be handled manually or mechanically in a simple manner and allows individual reagent carriers 4 to be detached from the interconnected row so that the remaining reagent carriers 4 in the interconnected row are still closed by the respective covers 2 and are thus protected.

It is immediately apparent that only an extremely small amount of material is required to produce such a reagent carrier composite 3 with protected test regions 8 i.e. the amount of material required for the interconnected row of covers. The row of covers as well as the individual reagent carriers are in one embodiment manufactured from a plastic e.g. in an injection-molding process. However, other materials can also be used to form the covers and/or the reagent carriers e.g. a multicomponent/composite material or coated material with good sealing properties.

The row of interconnected reagent carriers 3 shown in FIG. 1*b* contains for example 12 reagent carriers 4. This is a favorable size for handling the interconnected row of reagent carriers 3 during any packaging processes or in an analytical system.

If required more or fewer than 12 reagent carriers can be combined to form a row of interconnected reagent carriers.

Figure 3:
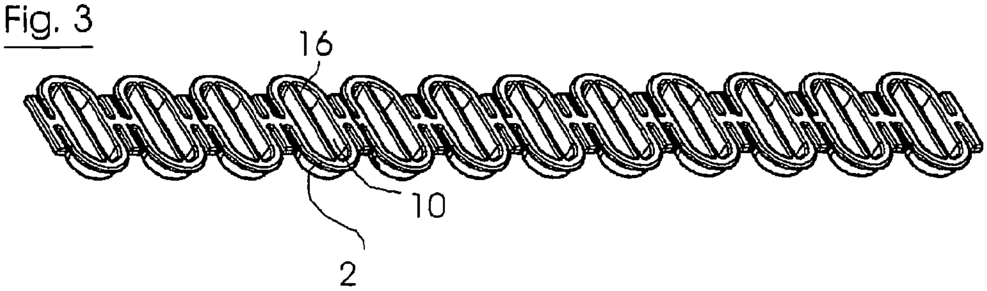
FIG. 3 shows a row of interconnected protective covers.

FIG. 3 shows a variant of the row of covers shown in FIG. 1*a*. The covers in FIG. 3 have a stabilizing cross-piece 16 on the concave rear-side of the bulges 10. Otherwise the covers 2 from FIG. 3 correspond to the covers from FIG. 1*a*.

Figure 4:
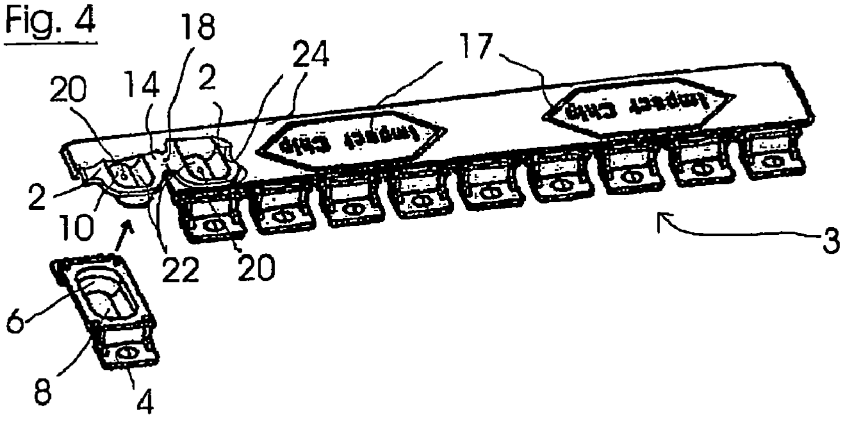
FIG. 4 shows in a perspective diagram a further embodiment example of a row of interconnected reagent carriers according to the invention in which one reagent carrier is shown detached from the interconnected row and an upper protective foil on the row of covers is shown partially torn away in order to show some details more clearly.

A further embodiment example of a row of interconnected reagent carriers according to the invention is shown in FIG. 4. The reagent carriers 4 in FIG. 4 correspond to the reagent carriers from FIG. 1*a*. The covers 2 in FIG. 4 correspond essentially to the covers 2 from FIG. 1*a*, but the two following differences should be noted. In FIG. 4 the individual covers 2 are joined together by connecting straps 14' where the connecting straps 14' have a weakened section of material for example in the form of a perforation strip which defines a predetermined breaking point 18. The predetermined breaking points 18 allow the row of interconnected reagent carriers 3 to be divided if required. This allows individual reagent carriers 4 with covers 2 to be separated in a simple manner from the interconnected row 3. The covers 2 in FIG. 4 have communication openings 20 in the bulges 10. The communication openings 20 connect the test region 8 of the respective reagent carrier 4 with the concave hollow space 22 on the rear-side of the bulge 10. The concave hollow spaces 22 can be used as reservoirs and can thus hold a desiccant and/or optionally reagents. These reservoirs 22 are sealed tight towards the outside by a sealing foil 24 which can be removed as required. The sealing foil 24 creates a flat surface on the interconnected row 3 on which information 17 can be easily printed.

Figure 5:
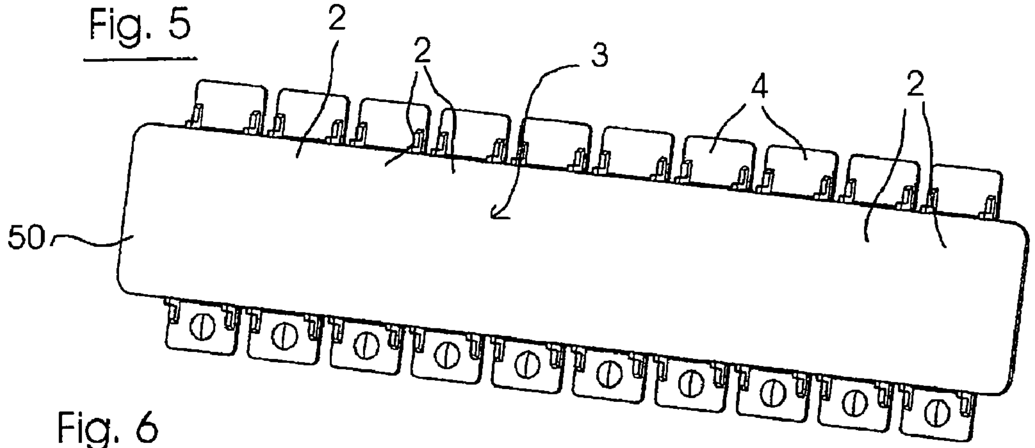
FIG. 5 shows a top-view of a further embodiment example of a row of interconnected reagent carriers according to the invention with a protective cover which is flat on the outside and thus a protective cover on which information can be easily printed.

A further embodiment example of a row of interconnected reagent carriers 3 according to the invention is shown in FIG. 5 in a top-view. The protective covers 2 for the reagent carriers 4 arranged side by side in a row are combined to form a common protective cover plate 50 which according to FIG. 6 and FIG. 7 has snap bars 52 which project downwards on their underside. The snap bars 52 are arranged parallel to one another where neighboring snap bars 52 are at a distance x from one another which approximately corresponds to the width d of the reagent carriers 4. The free ends of the snap bars 52 have a widened area 54 which defines an undercut and ensures that a reagent carrier 4 that is snapped in between two neighboring snap bars 52 is fastened securely and well-sealed on the cover plate 50. In this connection the widened area 54 of the respective snap bar 52 grips under an upper wall section 56 of the reagent carrier 4. The length y of the snap bars 52 corresponds essentially to the distance e between two opposing stop lugs 58 projecting downwards from the wall section 56 which in the snapped-in state receive one snap bar 52 lengthwise between them. In this manner the reagent carrier 4 is secured against shifting in the longitudinal direction of the snap bars 52.

Figure 6:
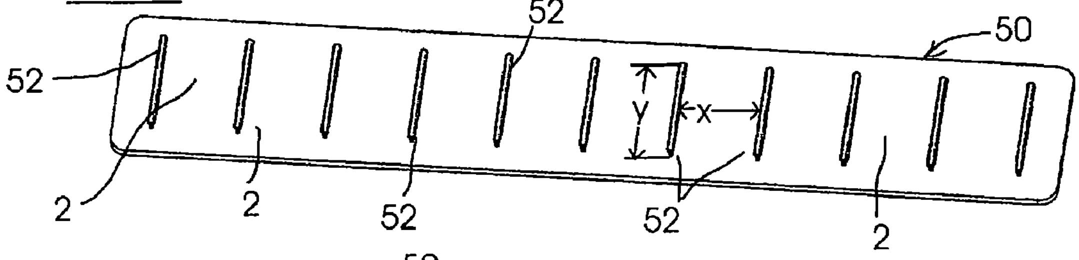
FIG. 6 shows the protective cover of the row of interconnected reagent carriers from FIG. 5 with a view of the underside of the protective cover.
Figure 7:
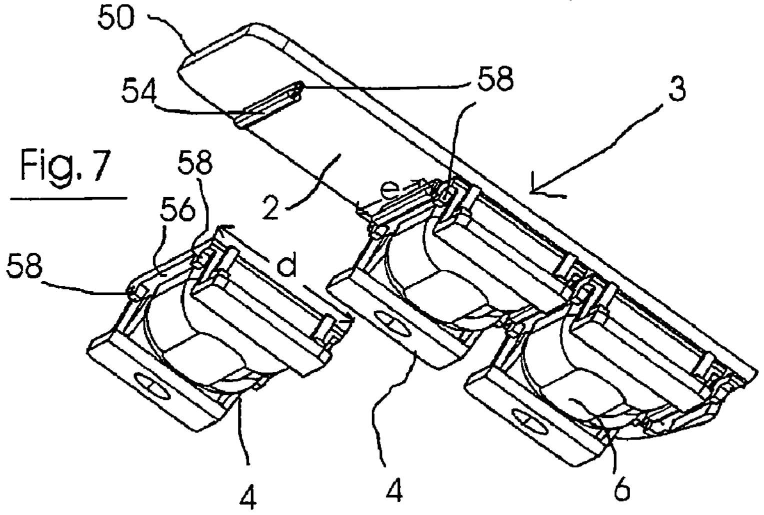
FIG. 7 shows a perspective diagram of a section of the row of interconnected reagent carriers from FIG. 5 in which one reagent carrier is shown detached from the interconnected row in order to allow some details to be more easily identified.

The cover according to FIG. 6 can have additional sealing elements or a more complicated sealing geometry which could ensure the test regions of the reagent carriers 4 are sealed with an even higher degree of certainty.

In the figures the rows of interconnected reagent carriers 3 are shown with reagent carriers 4 arranged side by side where the longest dimension of the reagent carriers 4 is aligned at right angles to the longitudinal direction of the interconnected row 3. In other embodiment examples other orientations are possible such as angled positions or a lengthwise alignment of the reagent carriers 4.

A magazine case 30 for strips of interconnected reagent carriers according to the invention is shown in FIGS. 8*a* and 8*b*. The magazine case 30 essentially has a cuboid shape with two opposing front sides 32, 34. A sliding closure 36 is provided on the front face 32 which is shown in FIG. 8*a* in a partially opened position. The opened sliding closure 36 releases a slide-in/slide-out opening 38 through which the magazine case 30 can be loaded with rows of interconnected reagent carriers 3. An opening 40 is provided on the front face 34 which allows a pushing tool to access the individual rows of interconnected reagent carriers 3 which can be used to push rows of interconnected reagent carriers 3 through the opening 38 to the outside.

Shelf-like stacking units 42 for the rows of interconnected reagent carriers 3 are provided in the interior of the magazine case 30 on opposing inner sides. The stacking units 42 form sliding guides along which the rows of interconnected reagent carriers 3 can be displaced in a longitudinal direction in order to for example push them out of the magazine case 30.

The dimensions of the magazine case 30 are such that it can hold a predetermined number of rows of interconnected reagent carriers in a stacked arrangement according to FIG. 8*a*, 8*b*. For transport and storage purposes the magazine case 30 loaded with the rows of interconnected reagent carriers 3 can additionally have an outer packaging such as a foil packaging.

The combination of a magazine case and rows of interconnected reagent carriers is a particularly advantageous aspect of the invention.

It should be noted that contrary to the single row connected arrangement 3 of reagent carriers 4 that are shown it is also possible according to the teaching of the invention to produce connected multiple row arrangements in the sense of two-dimensional reagent carrier fields. Furthermore a variant of the invention is conceivable in which the protective covers 2 are not arranged in a straight row as shown in FIG. 1*a* or FIG. 3 but are rather arranged and interconnected to form a ring such that the reagent carrier composite also forms a circular arrangement. In this connection according to one embodiment of the ring variant, it can be provided that the protective covers lie in a common plane and are oriented towards a common side.

According to another embodiment of the ring variant, the covers are arranged such that their outer sides are aligned radially relative to the centre of the ring. The reagent carriers in the composite are in one embodiment arranged radially on the outside of the covers.

Furthermore, the concept according to the invention for forming composites of reagent carriers can also be applied to the formation of composites of initially separate small containers for chemicals, drugs etc. by the interconnected assembly of their closure elements and especially covers and can thus be generalized.

What is claimed is:

1. A group of reagent carriers that is combined to form a composite, each one of which has at least one test region, wherein the reagent carriers each have a shallow trough-like depression containing the test regions which is closed from the outside by a protective cover and are held together in the composite exclusively by interconnected protective covers for the test regions, wherein the protective covers have hollow spaces for holding a desiccant and/or a component which is to be brought into contact with the reagent carriers.

2. The group of reagent carriers that is combined to form a composite according to claim 1, wherein the protective covers are interconnected to form a strip arrangement and the reagent carriers that are held together by the protective covers in the composite are arranged side-by-side to form a row corresponding to a strip arrangement.

3. The group of reagent carriers that is combined to form a composite according to claim 1, wherein the protective covers have a bulge having an approximately complementary contour to the contour of the trough-like depression, which extends into the trough-like depression.

4. The group of reagent carriers that is combined to form a composite according to claim 3, wherein the bulges define the hollow spaces for holding a desiccant and/or a component which is to be brought into contact with the reagent carriers.

5. The group of reagent carriers that is combined to form a composite according to claim 1, wherein the hollow spaces of the protective covers have communication openings or predetermined break-through points that can be pierced as required in the partitions separating them from the trough-like depressions.

6. The group of reagent carriers that is combined to form a composite according to claim 5, wherein the hollow spaces are sealed externally by a sealing foil.

7. The group of reagent carriers that is combined to form a composite according to claim 1, wherein the hollow spaces are sealed externally by a sealing foil.

8. The group of reagent carriers that is combined to form a composite according to claim 1, wherein the protective covers and the reagent carriers have mutually complementary and mutually engaging snap connection means or clamp connection means.

9. The group of reagent carriers that is combined to form a composite according to claim 1, wherein the protective covers and the reagent carriers have mutually complementary and mutually engaging sealing means.

10. The group of reagent carriers that is combined to form a composite according to claim 1, wherein predetermined breaking points are prepared in the connecting sites between the covers.

11. The group of reagent carriers that is combined to form a composite according to claim 1, wherein the composite has an essentially flat surface section with information printed thereon.

* * * * *